(12) United States Patent
Ishii

(10) Patent No.: US 6,680,033 B2
(45) Date of Patent: Jan. 20, 2004

(54) COMPOSITE DEODORIZATION SYSTEM AND ION DEODORIZATION SYSTEM

(75) Inventor: Hideaki Ishii, Takahagi (JP)

(73) Assignee: Asahi Environmental System Ltd., Tokyo (JP)

(*) Notice: Subject to any disclaimer, the term of this patent is extended or adjusted under 35 U.S.C. 154(b) by 161 days.

(21) Appl. No.: 09/911,128

(22) Filed: Jul. 23, 2001

(65) Prior Publication Data
US 2002/0030023 A1 Mar. 14, 2002

(30) Foreign Application Priority Data

Jul. 25, 2000 (JP) .................................. 2000-224550
Jul. 25, 2000 (JP) .................................. 2000-224551

(51) Int. Cl.[7] ............... A61L 9/00; B01J 19/08; B01J 10/00; F25D 17/06
(52) U.S. Cl. ............... 422/306; 422/307; 422/305; 422/186.07; 422/186.09; 422/187; 62/93; 62/95
(58) Field of Search ............... 422/1, 4, 5, 22, 422/23, 28–32, 186.03, 121, 186.07, 186.09, 186.1, 186.3, 187, 305–306; 62/93, 95

(56) References Cited

U.S. PATENT DOCUMENTS 4,093,430 A * 6/1978 Schwab et al.
4,780,277 A * 10/1988 Tanaka et al.
5,445,798 A * 8/1995 Ikeda et al.
5,681,533 A * 10/1997 Hiromi
6,071,481 A * 6/2000 Mathews et al.

FOREIGN PATENT DOCUMENTS

| DE | 198 38 107 A1 | 3/1999 |
| GB | 1029621 | 5/1966 |
| GB | 2 304 576 A | 3/1997 |
| JP | 03109953 A | 5/1991 |
| JP | 06262098 A | 9/1994 |
| JP | 09232068 A | 9/1997 |
| JP | 11060208 A | 3/1999 |

* cited by examiner

Primary Examiner—Robert J. Warden, Sr.
Assistant Examiner—Monzer R. Chorbaji
(74) Attorney, Agent, or Firm—Workman Nydegger

(57) ABSTRACT

A large amount of treated gas containing odor components is efficiently deodorized by performing ozone deodorization after water molecule deodorization, and thereafter performing ion deodorization. A composite deodorization system is provided with a first chamber for performing the water molecule deodorization connected with a fermentation system by a gas introduction opening supplied with the treated gas containing odor components from the fermentation system, a second chamber for performing ozone deodorization connected with the first chamber by a flow passage tube, a third chamber for performing ion deodorization connected with the second chamber by a connection tube, an ozone filter incorporated at a connection position of the second chamber and the connection tube, and a third chamber having a gas discharge opening for discharging the treated gas.

1 Claim, 4 Drawing Sheets

COMPOSITE DEODORIZATION SYSTEM AND ION DEODORIZATION SYSTEM

This application is based on patent application Ser. Nos. 2000-224550 filed Jul. 25, 2000 and 2000-224551 filed Jul. 25, 2000 in Japan, the content of which is incorporated hereinto by reference.

BACKGROUND OF THE INVENTION

1. Field of the Invention

The present invention relates to a composite deodorization method combining water molecule deodorization, ozone deodorization and ion deodorization methods, and a composite deodorization system, and to an ion deodorization system which ionizes the treated gas to negative ions and removes by adsorbing odor components to a photocatalyst panel thereby decomposing them by an oxidative decomposition reaction.

2. Description of the Related Art

Heretofore, as methods for deodorizing a gas containing odor components, there have been known a water molecule deodorization method, an ozone deodorization method, an ion deodorization method and the like. Each of these methods is for efficiently recovering odor components contained in the gas to achieve deodorization. The water deodorization method removes water in the gas thereby removing odor components dissolved in the water, the ozone deodorization method generates plasma ozone to decompose the odor components by oxidation thereby achieving deodorization. An air cleaner for removing odor components in a living room or the like using the ozone deodorization method is disclosed in, for example, Japanese Patent Application Laid-open No. 6-262098. According to the publication, it is described that air in the living room or the like is taken into the cleaner, deodorization and sterilization are performed by an ozone deodorization catalyst, and excess ozone is removed by an acid gas absorber.

The ion deodorization method is to ionize the gas to negative ions, absorb odor components in the gas to a photocatalyst, and decompose the odor components by oxidation. An air cleaner for removing odor components in a living room or the like using the ion deodorization method is disclosed in, for example, Japanese Patent Application Laid-open No. 3-109953. According to the publication, a method is described in which to a treated gas passing through a dust collection filter and a catalyst layer, corona discharge is used to ionize the gas to negative ions. These methods are to deodorize a treated gas of a predetermined amount in a closed space such as a living room or the like.

A photocatalytic action means that when oxygen or water vapor in the air contacts the photocatalyst, it changes into an active oxygen species by an optical energy, and harmful substances and active oxygen species repeat an oxidative decomposition reaction to decompose the harmful substances into water and carbon dioxide. For example, it is known that when interiors and exteriors are finished using a photocatalyst panel coated with a photocatalyst coating based on titanium oxide, staining-proof, sterilizing, mold-proof, and deodorization effects are obtained.

When performing air cleaning of a living room or the like utilizing the photocatalytic action, it is impossible to deodorize a predetermined amount of gas only by oxidative decomposition of odor components spontaneously adhering the photocatalyst. Then, a method is described in, for example, Japanese Patent Application Laid-open No. 11-60208, in which a photocatalyst panel provided with a photocatalyst coating of titanium oxide is irradiated with ultraviolet light to oxidize and reactivate the photocatalyst to promote the photocatalytic action. According to this publication, it is described that in ion and ozone generators having a needle-formed electrode and a cylindrical electrode, ultraviolet light is emitted from the needle-formed electrode and ion and ozone are generated to achieve deodorization. Further, a system to ionize the treated gas containing odor components to negative ions to cause odor components to forcedly absorb into the photocatalyst panel is described in, for example, Japanese Patent Application Laid-open No. 3-109953. According to this publication, a method is described in which a treated gas passing through a dust collection filter and a catalyst layer is negatively ionized using corona discharge. On the other hand, a method is known in which negative ions are emitted directly to the air in the treated gas. Of these, an electron radiator using an electron radiation needle is described in Japanese Patent Application Laid-open No. 9-232068.

On the other hand, in a fermentation system in which organic residues are treated to produce a compost, a large amount of gases containing odor components associated with aerobic fermentation are generated. When performing deodorization of large amounts of gas containing odor components, there has been a problem in that only by the water molecule deodorization method, only water-soluble odor components can be deodorized. Further, in the ozone deodorization method, in view of the global environment protection, in order to treat the generated ozone, an apparatus for treating a large amount of gas results in a cost increase. Further, there has been a problem in that only by the ion deodorization method, only odor components spontaneously adhering to the photocatalyst are oxidatively decomposed, and to deodorize a large amount of gas, photocatalyst of large surface area is required which makes the apparatus large-sized.

With an eye on the deodorization function in the ion deodorization method, only by installation of a photocatalyst panel, only odor components spontaneously adhering to the photocatalyst panel are oxidatively decomposed, and therefore it is impossible to forcedly deodorize a large amount of air containing odor components. Even when the photocatalyst panel is irradiated with ultraviolet light to promote the photocatalyst, the deodorization capacity is limited as far as with the photocatalyst panel of a constant surface area.

Then, it is performed that the treated gas is negatively ionized by corona discharge to cause odor components to adhere forcedly to the photocatalyst panel, however, since the method using corona discharge is low in negative ion production capacity, there has been a problem in that the capacity of forcedly adhering odor components to the photocatalyst panel is low. On the other hand, in the method using corona discharge, since ozone is generated, there is a problem in that the oxidative decomposition reaction of the photocatalyst is disturbed. Further, in view of the global environment protection, a treatment is necessary for preventing release of ozone out of the system which results in a large-sized deodorization system and an increased cost.

SUMMARY OF THE INVENTION

An object of the present invention is to provide a composite deodorization method in which ozone deodorization is performed after water molecule deodorization, and then ion deodorization is performed to efficiently deodorize a large amount of treated gas containing odor components and a system for the method.

Another object of the present invention is to provide an ion deodorization system in which negative ions are radiated directly to the treated gas to promote adherence of odor components to the photocatalyst so that in combination with promotion of the photocatalyst by ultraviolet radiation, a large amount of odor is efficiently removed.

The present invention which attains the above objects is characterized by comprising a water molecule deodorization step for removing water from a treated gas so that odor components dissolved in the water in the treated gas are removed; an ozone deodorization step for mixing the treated gas treated in the water molecule deodorization step with plasma ozone and oxidatively decomposing odor components contained in the treated gas; and an ion deodorization step for negatively ionizing the treated gas treated in the ozone deodorization step and adhering odor components contained in the treated gas for oxidative decomposition.

Further, the water molecule deodorization step is possible to include a radiation treatment step for decreasing temperature of the treated gas removed of odor components.

Still further, the ozone deodorization step is possible to include an ozone removing step for removing plasma ozone contained in the treated gas oxidatively decomposed of odor components.

Yet further, the present invention is characterized by comprising a first chamber having a gas introduction opening supplied with a treated gas, a second chamber communicating with the first chamber, and a third chamber communicating with the second chamber, wherein the first chamber includes a cooling panel for condensing water in the treated gas and a drain panel for discharging water drops condensed on the cooling panel along with odor components dissolved in water in the treated gas, and the second chamber includes an ozone generator for generating plasma ozone and a reaction chamber for oxidatively decomposing odor components contained in the treated gas by the plasma ozone generated by the ozone generator, and the third chamber includes an electron radiator for negatively ionizing the treated gas, a photocatalyst panel for adsorbing and oxidatively decomposing odor components contained in the treated gas, and a gas discharge opening for discharging the treated gas. In addition, relative humidity of the treated gas treated by the cooling panel is lower than external humidity of the first chamber.

Further, the first chamber can include a heat radiation panel for decreasing temperature of the treated gas passed through the cooling panel. In addition, temperature of the treated gas treated by the heat radiation panel is lower than external temperature of the first chamber.

The first chamber and the second chamber are connected with a flow passage tube, and an ozone generator can be disposed at the connection position of the first chamber and the flow passage tube. Further, the second chamber can include an ozone removing filter for removing ozone contained in the treated gas.

The electron radiator radiates electrons directly to the space for negatively ionizing the treated gas. Further, the third chamber can include an ultraviolet irradiator for irradiating ultraviolet light to the photocatalyst panel.

Yet further, the treated gas is a gas generated during aerobic fermentation of organic residue.

Yet further, the present invention is an ion deodorization system for absorbing odor components contained in the treated gas and removing the odor components by an oxidative decomposition reaction, characterized by comprising an electron radiator for negatively ionizing the treated gas, and an ultraviolet irradiator for irradiating ultraviolet light to the photocatalyst panel. In addition, the electron radiator radiates electrons directly to the space for negatively ionizing the treated gas.

Yet further, the present invention is an ion deodorization system for absorbing odor components contained in the treated gas and removing the odor components by an oxidative decomposition reaction, characterized by comprising an electron radiator for negatively ionizing the treated gas, wherein the electron radiator radiates electrons directly to the space, thereby negatively ionizing the treated gas.

The above and other objects, effects, features and advantages of the present invention will become more apparent from the following description of embodiments thereof taken in conjunction with the accompanying drawings.

DETAILED DESCRIPTION OF PREFERRED EMBODIMENTS

In the following, an embodiment of the present invention will be described in detail with reference to the drawings.

Figure 1:
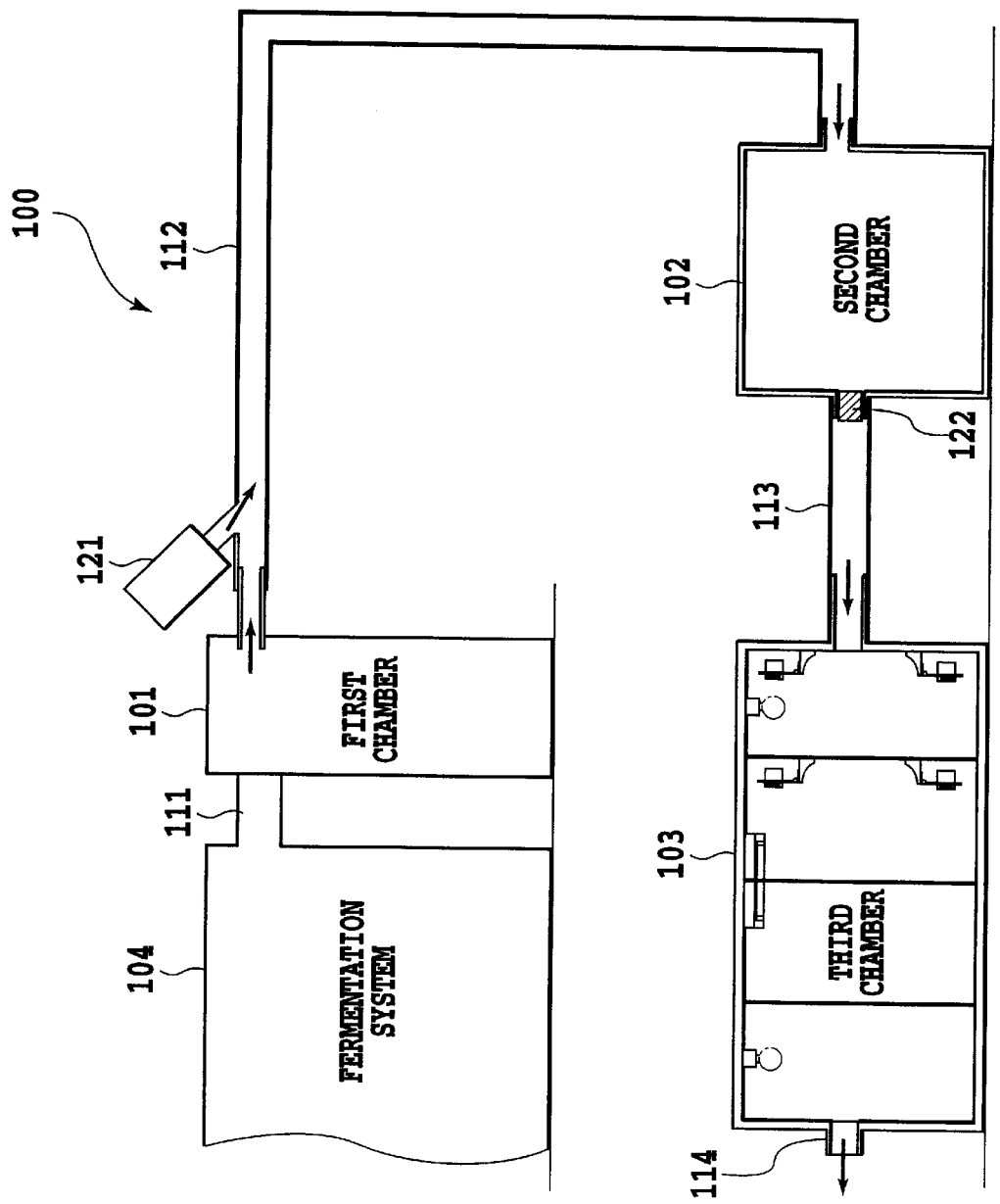
FIG. 1 is a construction diagram showing the composite deodorization system according to an embodiment of the present invention.

FIG. 1 shows the brief construction of the composite deodorization system according to the embodiment of the present invention. A composite deodorization system 100 comprises a first chamber 101 for performing water molecule deodorization, a second chamber 102 for performing ozone deodorization, and a third chamber 103 for performing ion deodorization. The first chamber 101 is connected with a fermentation system 104 by a gas introduction opening 111 supplied with a treated gas containing odor components from the fermentation system 104. The first chamber 101 and the second chamber 102 are connected with a flow passage tube 112, and an ozone generator 121 is disposed at the connection position of the first chamber 101 and the flow passage tube 112. The second chamber 102 and the third chamber 103 are connected with a connection tube 113, and an ozone filter 122 is incorporated at the connection position of the second chamber 102 and the connection tube 113. The third chamber 103 is provided with a gas discharge opening 114 for discharging the treated gas.

With such a construction, the treated gas containing odor components flowed in from the gas introduction opening 111 of the first chamber 101 is, in the first chamber 101, water is removed by condensation, and odor components dissolved in water of the treated gas are discharged at the same time. As for oxidative decomposition reaction by ozone and a photocatalyst, the odor components themselves are higher in decomposition ability than odor components coupled to water molecule. Further, when condensation occurs on the porous surface of the photocatalyst, there is a problem in that oxidative decomposition ability is inferior. Then, prior to the second chamber 102 for performing ozone deodorization and the third chamber 103 for performing ion deodorization, by performing water molecule deodorization for dehumidifying the treated gas, it is possible to enhance the oxidative decomposition ability of ozone and the photocatalyst.

The treated gas treated in the first chamber 101 is conducted to the flow passage tube 112 for connecting the first chamber 101 and the second chamber 102. Ozone generated from the ozone generator 121 disposed at the connection position of the first chamber 101 and the flow passage tube 112, in a reaction chamber comprising the flow passage tube 112 and the second chamber 102, contacts the treated gas to remove the odor components by oxidative decomposition.

The treated gas treated in the second chamber 102 is conducted to the connection tube 113 for connecting the second chamber 102 and the third chamber 103. At the connection position of the second chamber 102 and the connection tube 113, an ozone filter 122 is incorporated, which, from the treated gas treated in the second chamber 102, removes residual ozone. Ozone has a problem of disturbing oxidative decomposition of the photocatalyst, and emission of ozone from the composite deodorization system 100 is not desirable from the global environment protection point of view. Then, prior to the third chamber 103 for performing ion deodorization, by disposing an ozone filter 122, such a problem can be solved.

The treated gas treated in the second chamber 102 is conducted into the third chamber 103, where odor components are oxidatively decomposed and removed by the photocatalyst. Since, to treat a large amount of gas, it is necessary to adhere odor components forcedly to the photocatalyst panel, the treated gas is negatively ionized, which will be described in detail later. The treated gas treated in the third chamber 103 is discharged from the gas discharge opening 114.

Figure 2:
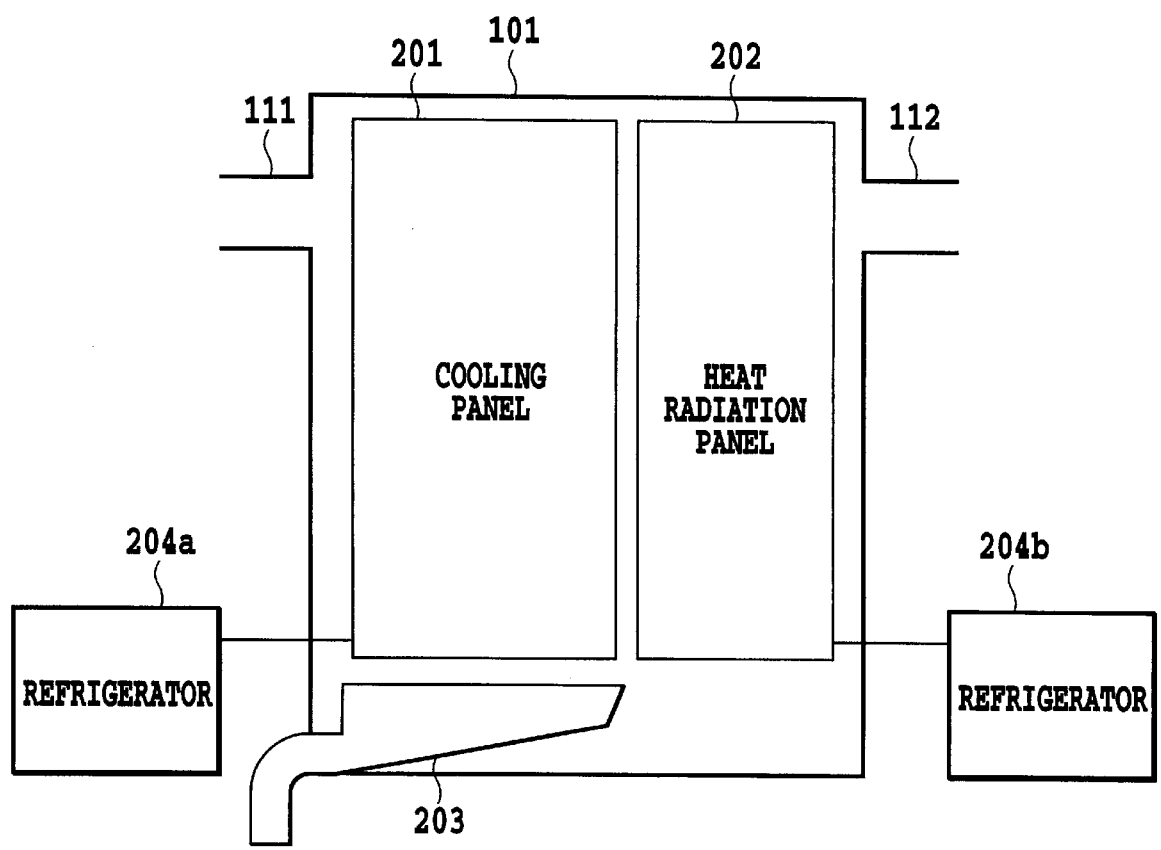
FIG. 2 is a construction diagram showing a first chamber of the composite deodorization system according to the embodiment of the present invention.

FIG. 2 shows the construction of the first chamber of the composite deodorization system according to an embodiment of the present invention. The first chamber 101 comprises a cooling panel 201 for cooling the treated gas to cause condensation, a heat radiation panel 202 for decreasing temperature of the treated gas, a drain panel 203 for discharging condensed water, and refrigerators 204a and 204b for cooling the cooling panel 201 and the heat radiation panel 202.

With such a construction, the treated gas containing odor components flowed in from the gas introduction opening 111 of the first chamber 101 is, in the first chamber 101 is cooled by the cooling panel 201 to condense water on the cooling panel 201. Odor components dissolved in water of the treated gas are discharged and removed along with condensed water from the drain panel 203. Further, since the lower the temperature, the better the oxidative decomposition efficiency of ozone deodorization, a heat radiation panel 202 is provided to decrease the temperature of the treated gas. Temperature of the treated gas discharged from the flow passage tube 112 is cooled to below the external temperature of the environment in which the composite deodorization system according to the present embodiment is disposed. Further, as described above, to enhance the oxidative decomposition ability of ozone and photocatalyst, humidity of the treated gas from the flow passage tube 112 is dehumidified to below the external humidity in the environment in which the composite deodorization system according to the present embodiment is disposed. The treated gas treated in the first chamber 101 is conducted to the flow passage tube 112.

Figure 3A:
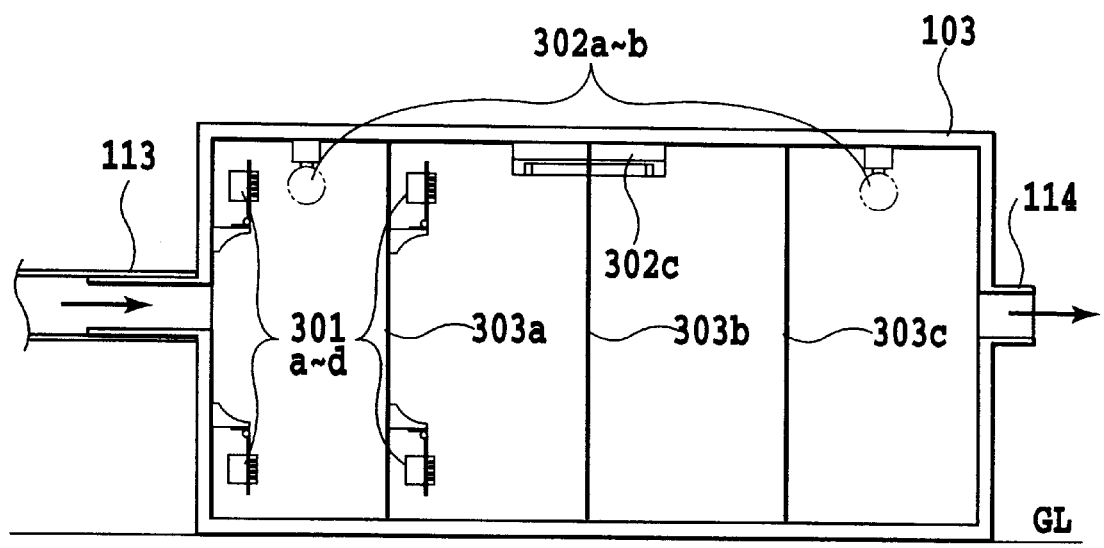
FIG. 3A is a side diagram showing a third chamber of the composite deodorization system according to the embodiment of the present invention.
Figure 3B:
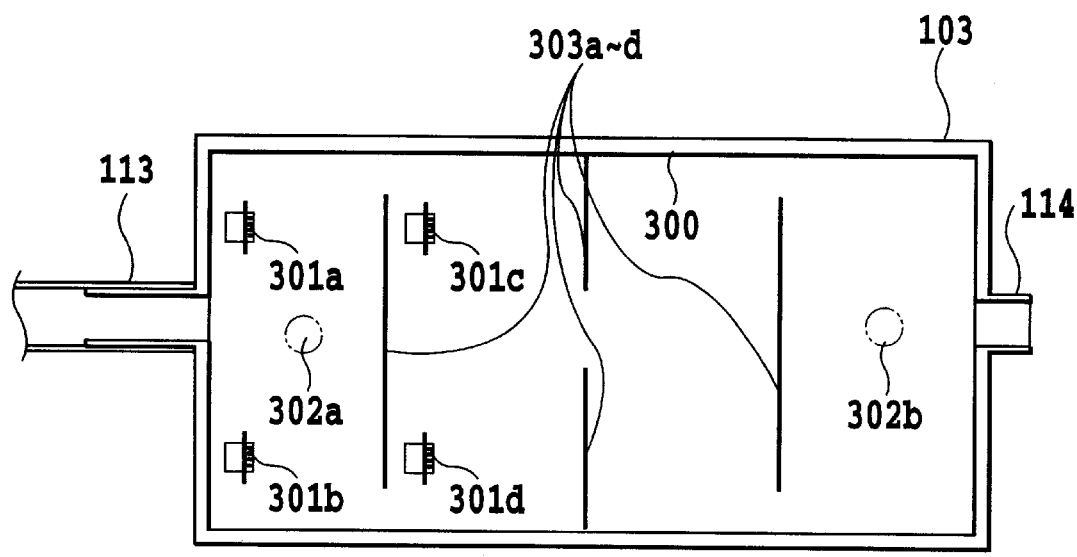
FIG. 3B is a top diagram showing the third chamber of the composite deodorization system according to the embodiment of the present invention.

FIG. 3A and FIG. 3B show the construction of the third chamber of the composite deodorization system according to an embodiment of the present invention. The third chamber 103 comprises a photocatalyst panel 300 for oxidatively decomposing odor components, electron radiators 301a to 301d for emitting negative ions, ultraviolet radiation lamps 302a to 302c for oxidatively reactivating the photocatalyst, and partition plates 303a to 303c for disturbing air flow passage in the inside. The photocatalyst panel is provided on the entire wall surface in the third chamber and wall surfaces of the partition plates 303a to 303d.

With such a construction, the treated gas treated in the second chamber 102 flows from the connection tube 113 into the third chamber 103 and negatively ionized by electrons radiated directly from the electron radiators 301a to 301d. Negatively ionized odor components are adsorbed by the photocatalyst panel 300 and decomposed by an oxidative decomposition reaction. The treated gas treated in the third chamber 103 is discharged from the gas discharge opening 114. The ultraviolet lamps 302a to 302c promote oxidative reactivation of the photocatalyst of the photocatalyst panel 300. The partition plates 303a to 303d are to disturb air flow passage inside the third chamber 103 to promote contact of the treated gas with the photocatalyst panel 300.

According to the present embodiment, since the treated gas is negatively ionized by the electron radiators 301a to 301d, negatively ionized odor components can be forcedly adhered to the photocatalyst panel 300. Further, since the treated gas is negatively ionized by emitting electrons directly from the electron radiators 301a to 301d, ozone is not generated. Therefore, since the oxidative reactivation reaction of the photocatalyst panel 300 is not disturbed, and no ozone is emitted, it has a useful effect from the point of view of global environment protection.

Figure 4:
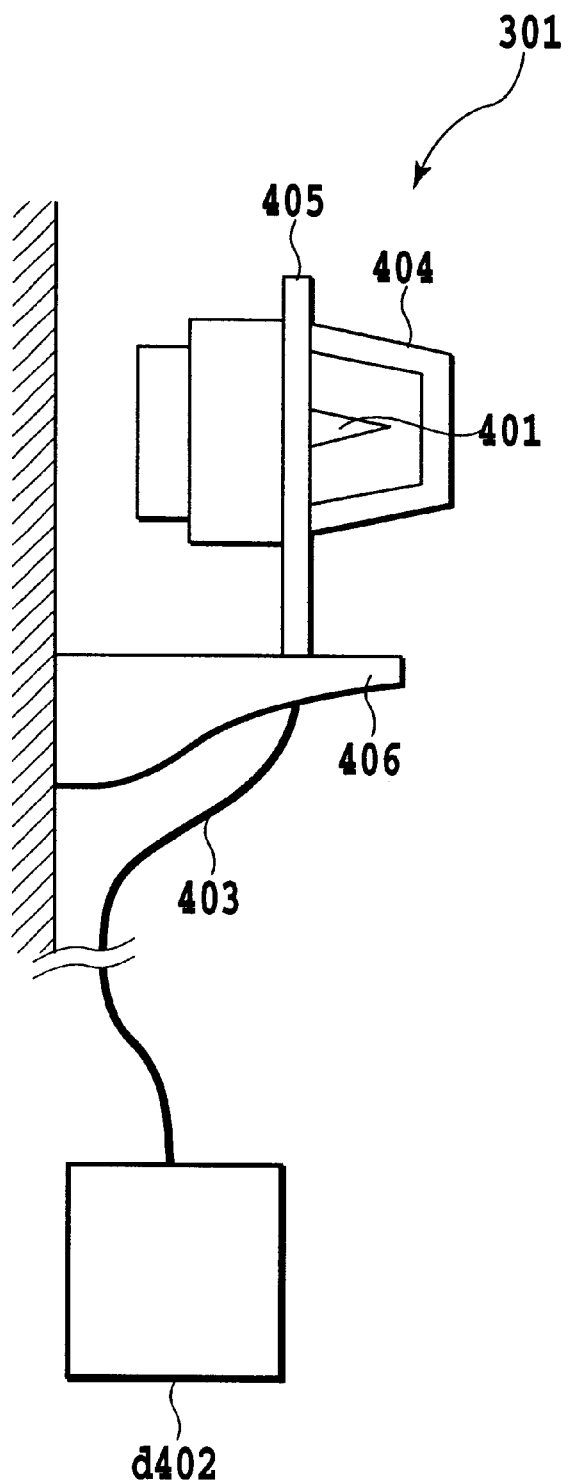
FIG. 4 is a block diagram showing hardware construction of an electron radiator.

FIG. 4 shows hardware construction of the electron radiator. The electron radiator 301 is described in Japanese Patent Application Laid-open No. 9-232068 previously disclosed by the present applicant. The electron radiator 301 comprises an electron radiation needle 401 for emitting negative ions, an ion generator 402 for supplying the electron radiation needle 401 with electrons, and an electron conductor wire 403 for connecting the electron radiation needle 401 and the ion generator 402. Further, an electron jet louver for protecting the electron radiation needle 401 and a mounting piece 405 are provided and disposed on a mounting base structure 406 or the like.

With such a construction, the electron radiator 301 generates a high voltage of several thousand volts by the ion generator 402, and conducts this voltage to the electron radiation needle 401 by the electron conductor wire 403. The electron radiation needle 401 corresponds to a negative electrode. By opening a positive electrode, electrons are emitted from the electron radiation needle 403 and the emitted electrons go forward while hitting electrons of air molecule, generating an electron avalanche phenomenon in the vicinity of the electron jet louver 404.

An exhaust deodorization apparatus of a fermentation system for producing compost by treating organic wastes using the composite deodorization system according to the present invention will be described. The exhaust deodorization apparatus, considering deodorization of treated gas of about 100 m$^3$ per minute, has a volume of the first chamber 101 of about 220 m$^3$, a volume of the second chamber 102 of about 1000 m$^3$, and a volume of the third chamber 103 of about 1400 m$^3$. The exhaust deodorization apparatus comprises 150 kW refrigerators 204a and 204b, 660 plasma ozone tubes as the ozone generator 121, 500 electron radiators 301 (more than 3 million ion molecules/cc/moment), and 100 units of 150W ultraviolet lamps 302, and the surface area of the photocatalyst panel 300 in the third chamber 103 is about 14,000 m$^2$. Results of deodorization experiment conducted using the above exhaust deodorization apparatus are shown in Table 1 and Table 2.

TABLE 1 unit: ppm

| Odor Component | Fermentation system outlet | Present system outlet | System boundary | Prevention act reference value |
|---|---|---|---|---|
| Ammonia | 360 | 6.4 | <0.1 | 1 |
| Hydrogen sulfide | 0.03 | <0.02 | <0.002 | 0.02 |
| Methyl mercaptan | 0.36 | <0.002 | <0.0002 | 0.002 |
| Methyl sulfide | 3.8 | 0.01 | <0.001 | 0.01 |
| Dimethyl sulfide | 0.015 | <0.002 | <0.0009 | 0.009 |

Table 1 summarizes 5 items of malodor measurement results. It has been confirmed that measured values at the boundary of the fermentation system and the exhaust deodorization apparatus are much lower than the malodor prevention reference value.

TABLE 2

Measurement method: 3-point comparative odor bag method

| | Fermentation system outlet | Present system outlet | System boundary | Guidance reference value |
|---|---|---|---|---|
| Sensed odor concentration | 31000 | 170 | <10 | 80 |

Table 2 shows measurement results by the 3-point comparative odor bag method. The 3-point comparative odor bag method is a method for measuring an odor index by air dilution. Also in this case, it has been confirmed that measured values at the boundary of the fermentation system and the exhaust deodorization apparatus are much lower than the administrative guidance reference value.

In the present embodiment, the above experimental system has been described. The present invention can be applied by varying various parameters in the plant of organic waste treatment system or the like, from a system for deodorizing treated gas of about 100 m$^3$ per minute to a household air cleaner for deodorizing treated gas of 0.1 m$^3$ per minute.

The present invention has been described in detail with respect to preferred embodiments, and it will now be apparent from the foregoing to those skilled in the art that changes and modifications may be made without departing from the invention in its broader aspects, and it is the intention, therefore, in the appended claims to cover all such changes and modifications as fall within the true spirit of the invention.

What is claimed is:

1. A composite deodorization system comprising:
    a first chamber including: a gas introduction opening supplied with a treated gas, a cooling panel for condensing water in said treated gas, a drain panel for discharging water drops condensed on said cooling panel along with odor components dissolved in water in said treated gas, and a heat radiation panel for decreasing temperature of said treated gas passed through said cooling panel;
    an ozone generator disposed at a connection position of said first chamber and a flow passage tube, said ozone generator generates plasma ozone;
    a second chamber connected with said flow passage tube, said second chamber including a reaction chamber for oxidatively decomposing odor components contained in said treated gas by plasma ozone generated by said ozone generator;
    an ozone removing filter disposed at a connection position of said second chamber and a connection tube, said ozone removing filter removing ozone contained in said treated gas; and
    a third chamber connected with said connection tube, said third chamber including: an electron radiator which radiate electrons directly from an electron radiation needle to a space for negatively ionizing said treated gas, a photocatalyst panel for adsorbing and oxidatively decomposing odor components contained in said treated gas, an ultraviolet irradiator for irradiating ultraviolet light to said photocatalyst panel, and a gas discharge opening for discharging said treated gas.

* * * * *